(12) United States Patent
Lee et al.

(10) Patent No.: US 7,806,077 B2
(45) Date of Patent: *Oct. 5, 2010

(54) PLASMA NOZZLE ARRAY FOR PROVIDING UNIFORM SCALABLE MICROWAVE PLASMA GENERATION

(75) Inventors: Sang Hun Lee, Austin, TX (US); Jay Joongsoo Kim, San Jose, CA (US)

(73) Assignees: Amarante Technologies, Inc., San Jose, CA (US); Saian Corporation, Wakayama-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/902,435

(22) Filed: Jul. 30, 2004

(65) Prior Publication Data

US 2006/0021581 A1     Feb. 2, 2006

(51) Int. Cl.
- *C23F 1/00* (2006.01)
- *C23C 16/00* (2006.01)
- *H01L 21/306* (2006.01)

(52) U.S. Cl. .................. 118/723 MW; 156/345.36; 156/345.41

(58) Field of Classification Search ......... 118/723 MW; 156/345.36, 345.41; 219/121.48, 121.5
See application file for complete search history.

(56) References Cited

U.S. PATENT DOCUMENTS

| | | | | |
|---|---|---|---|---|
| 3,353,060 | A | * | 11/1967 | Yamamoto et al. ..... 315/111.31 |
| 3,417,287 | A | * | 12/1968 | Murayama ............. 315/111.11 |
| 4,185,213 | A | * | 1/1980 | Scannell ..................... 310/11 |
| 4,207,286 | A | | 6/1980 | Gut Boucher |
| 4,378,806 | A | * | 4/1983 | Henley-Cohn ............... 450/80 |
| 4,976,920 | A | | 12/1990 | Jacob |
| 5,084,239 | A | | 1/1992 | Moulton et al. |
| 5,170,098 | A | | 12/1992 | Dutton et al. |

(Continued)

FOREIGN PATENT DOCUMENTS

DE    44 08 301 A    9/1994

(Continued)

OTHER PUBLICATIONS

K. Kelly-W et al., "Room Temperature Sterilization of Surfaces and Fabrics With a One Atmosphere Uniform Glow Discharge Plasma", Journal of Industrial Microbiology & Biotechnology, 1998, pp. 69-74, vol. 20, Society for Industrial & Microbiology.

(Continued)

*Primary Examiner*—Parviz Hassanzadeh
*Assistant Examiner*—Rakesh Dhingra
(74) *Attorney, Agent, or Firm*—Smith Patent Office

(57) ABSTRACT

Microwave plasma nozzle array systems and methods for configuring the microwave plasma nozzle arrays are disclosed. The microwaves are transmitted to a microwave cavity in a specific manner and form an interference pattern that includes high-energy regions within the microwave cavity. The high-energy regions are controlled by the phases and the wavelengths of the microwaves. A plurality of nozzle elements is provided in the array. Each of the nozzle elements has a portion partially disposed in the microwave cavity and receives a gas for passing therethrough. The nozzle elements receive microwave energy from one of the high-energy regions. Each of the nozzle elements include a rod-shaped conductor having a tip that focuses the microwaves and a plasma is then generated using the received gas.

19 Claims, 11 Drawing Sheets

U.S. PATENT DOCUMENTS

| | | | |
|---|---|---|---|
| 5,188,862 A * | 2/1993 | Itatani et al. | 427/570 |
| 5,449,412 A * | 9/1995 | Pinneo | 118/723 MP |
| 5,503,676 A | 4/1996 | Shufflebotham et al. | |
| 5,565,118 A * | 10/1996 | Asquith et al. | 219/121.57 |
| 5,573,682 A | 11/1996 | Beason, Jr. et al. | |
| 5,741,460 A | 4/1998 | Jacob et al. | |
| 5,750,072 A | 5/1998 | Sangster et al. | |
| 5,825,485 A | 10/1998 | Cohn et al. | |
| 5,843,236 A * | 12/1998 | Yoshiki et al. | 118/723 MR |
| 5,869,401 A | 2/1999 | Brunemeier et al. | |
| 5,928,527 A | 7/1999 | Li et al. | |
| 5,938,854 A | 8/1999 | Roth | |
| 5,961,921 A | 10/1999 | Addy et al. | |
| 5,977,715 A | 11/1999 | Li et al. | |
| 5,980,768 A | 11/1999 | Abraham | |
| 6,016,766 A | 1/2000 | Pirkle et al. | |
| 6,017,825 A | 1/2000 | Kim et al. | |
| 6,030,579 A | 2/2000 | Addy et al. | |
| 6,068,817 A | 5/2000 | Addy et al. | |
| 6,080,270 A | 6/2000 | Tabrez et al. | |
| 6,165,910 A | 12/2000 | Flanner et al. | |
| 6,170,668 B1 | 1/2001 | Babko-Malyi | |
| 6,200,651 B1 | 3/2001 | Roche et al. | |
| 6,209,551 B1 | 4/2001 | Yang et al. | |
| 6,221,268 B1 | 4/2001 | Li et al. | |
| 6,221,792 B1 | 4/2001 | Yang et al. | |
| 6,225,593 B1 | 5/2001 | Howieson et al. | |
| 6,228,330 B1 | 5/2001 | Herrmann et al. | |
| 6,235,640 B1 | 5/2001 | Ebel et al. | |
| 6,309,979 B1 | 10/2001 | Patrick et al. | |
| 6,337,277 B1 | 1/2002 | Chou et al. | |
| 6,363,882 B1 | 4/2002 | Hao et al. | |
| 6,410,451 B2 | 6/2002 | Nguyen et al. | |
| 6,441,554 B1 | 8/2002 | Nam et al. | |
| 6,573,731 B1 | 6/2003 | Verdeyen et al. | |
| 6,635,997 B2 * | 10/2003 | Ikeda et al. | 315/111.21 |
| 6,652,709 B1 * | 11/2003 | Suzuki et al. | 156/345.41 |
| 6,677,550 B2 | 1/2004 | Fornsel et al. | |
| 6,696,662 B2 * | 2/2004 | Jewett et al. | 219/121.48 |
| 6,727,148 B1 | 4/2004 | Setton | |
| 6,792,742 B2 | 9/2004 | Ekkert | |
| 7,164,095 B2 * | 1/2007 | Lee et al. | 219/121.5 |
| 2003/0000823 A1 * | 1/2003 | Uhm et al. | 204/157.43 |
| 2005/0127068 A1 * | 6/2005 | Tang et al. | 219/700 |

FOREIGN PATENT DOCUMENTS

| | | | |
|---|---|---|---|
| DE | 101 64 120 A | | 7/2003 |
| GB | 0792085 A | * | 8/1997 |
| JP | 43-24312 B | | 10/1968 |
| JP | 63-50478 A | | 3/1988 |
| JP | 03-70375 A | | 3/1991 |
| JP | 03-241739 A | | 10/1991 |
| JP | 05-82449 A | | 4/1993 |
| JP | 05-275191 A | | 10/1993 |
| JP | 06-5384 A | | 1/1994 |
| JP | 06-263120 A | | 9/1994 |
| JP | 07-40056 A | | 2/1995 |
| JP | 07-153593 A | | 6/1995 |
| JP | 08-508362 A | | 9/1996 |
| JP | 08-319553 A | | 12/1996 |
| JP | 11-8093 A | | 1/1999 |
| JP | 11-21496 A | | 1/1999 |
| JP | 11-224795 A | | 8/1999 |
| JP | 2000-150484 A | | 5/2000 |
| JP | 2000-353689 A | | 12/2000 |
| JP | 2001-54556 A | | 2/2001 |
| JP | 2001-281284 A | | 10/2001 |
| JP | 2003-135571 A | | 5/2003 |
| JP | 2003-210556 A | | 7/2003 |
| JP | 2004-45262 A | | 12/2004 |
| WO | WO 98/35618 A | | 8/1998 |
| WO | WO 99/04606 A | | 1/1999 |
| WO | WO 01/06268 A | | 1/2001 |
| WO | WO 01/06402 A | | 1/2001 |
| WO | WO 01//43512 A | | 6/2001 |

OTHER PUBLICATIONS

T. Wu et al., "A Large-Area Plasma Source Excited by a Tunable Surface Wave Cavity", Review of Scientific Instruments, May 1999, pp. 2331-2337, vol. 70, No. 5, American Institute of Physics.

K. Kelly-W et al., "Use of a One Atmosphere Uniform Glow Discharge Plasma to Kill a Broad Spectrum of Microorganisms", Journal of Vacuum Science Technology, Jul./Aug. 1999, pp. 1539-1544, vol. 17 No. 4, American Vacuum Society.

I. Sorosnenko et al., "Sterilization of Medical Products in Low-Pressure Glow Discharges", Plasma Physics Reports, 2000, pp. 792-800, vol. 26, No. 9, MAIK "Nauka/Interperiodica".

J. Gerling, "Waveguide Components and Configurations for Optimal Performance in Microwave Hearing Systems", 2000, pp. 1-8, Gerling Applied Engineering, Inc.

P. Woskov et al., "Large Electrodless Plasmas at Atmospheric Pressure Sustained by a Microwave Waveguide", Plasma Science and Fusion Center, Massachusetts Institute of Technology, Jan. 2002, pp. 1-8, to be published in IEEE Transactions on Plasma Science.

S. Moon et al., "Characteristics of an Atmospheric Microwave-Induced Plasma Generated in Ambient Air by an Argon Discharge Excited in an Open-Ended Dielectric Discharge Tube", Physics of Plasmas, Sep. 2002, pp. 4045-4051, vol. 9, No. 9, American Institute of Physics.

J. Gerling, "Equipment and Methods for Waveguide Power Measurements in Microwave Heating Applications", 2002, pp. 1-8, Gerling Applied Engineering, Inc.

C. Kuruger et al., "Nonequilibrium Discharges in Air and Nitrogen Plasmas at Atmospheric Pressure", Pure Applied Chemistry, 2002, pp. 337-347, vol. 74, No. 3, IUPAC.

D. Korzec et al., "Free-Standing Microwave Excited Plasma Beam", Plasma Sources Science and Technology, Aug. 2003, pp. 523-532, vol. 12, Institute of Physics Publishing.

B. Park et al., "Sterilization Using a Microwave-Induced Argon Plasma System at Atmospheric Pressure", Physics of Plasmas, Nov. 2003, pp. 4539-4544, vol. 10, No. 11, American Institute of Physics.

V. Khomich et al., "Investigation of Principal Factors of the Sterilization by Plasma DC Glow Discharge", Institute of Physics NAS Ukraine, Ukraine.

* cited by examiner

FIG. 2

| Insertion Length of Conductor (mm) | S31[dB] | S31[%] |
|---:|---:|---:|
| 37 | -7.71 | 17% |
| 35 | -4.7 | 34% |
| 28 | -4.54 | 35% |
| 22 | -4.93 | 32% |
| 14 | -8.46 | 14% |
| 6 | -15.8 | 3% |

PLASMA NOZZLE ARRAY FOR PROVIDING UNIFORM SCALABLE MICROWAVE PLASMA GENERATION

CROSS REFERENCE TO RELATED APPLICATIONS

This application is related to concurrently filed U.S. application Ser. No. 10/902,433, filed on Jul. 30, 2004, entitled "SYSTEM AND METHOD FOR CONTROLLING A POWER DISTRIBUTION WITHIN A MICROWAVE CAVITY" which is hereby incorporated by reference in its entirety.

BACKGROUND OF THE INVENTION

1. Field of the Invention

The present invention relates to plasma generating systems, and more particularly to microwave plasma systems having plasma nozzle arrays.

2. Discussion of the Related Art

In recent years, the progress on producing plasma has been increasing. Typically, plasma consists of positive charged ions, neutral species and electrons. In general, plasmas may be subdivided into two categories: thermal equilibrium and thermal non-equilibrium plasmas. Thermal equilibrium implies that the temperature of all species including positive charged ions, neutral species, and electrons, is the same.

Plasmas may also be classified into local thermal equilibrium (LTE) and non-LTE plasmas, where this subdivision is typically related to the pressure of the plasmas. The term "local thermal equilibrium (LTE)" refers to a thermodynamic state where the temperatures of all of the plasma species are the same in the localized areas in the plasma.

A high plasma pressure induces a large number of collisions per unit time interval in the plasma, leading to sufficient energy exchange between the species comprising the plasma, and this leads to an equal temperature for the plasma species. A low plasma pressure, on the other hand, may yield one or more temperatures for the plasma species due to insufficient collisions between the species of the plasma.

In non-LTE, or simply non-thermal plasmas, the temperature of the ions and the neutral species is usually less than 100° C., while the temperature of electrons can be up to several tens of thousand degrees in Celsius. Therefore, non-LTE plasma may serve as highly reactive tools for powerful and also gentle applications without consuming a large amount of energy. This "hot coolness" allows a variety of processing possibilities and economic opportunities for various applications. Powerful applications include metal deposition systems and plasma cutters, and gentle applications include plasma surface cleaning systems and plasma displays.

One of these applications is plasma sterilization, which uses plasma to destroy microbial life, including highly resistant bacterial endospores. Sterilization is a critical step in ensuring the safety of medical and dental devices, materials, and fabrics for final use. Existing sterilization methods used in hospitals and industries include autoclaving, ethylene oxide gas (EtO), dry heat, and irradiation by gamma rays or electron beams. These technologies have a number of problems that must be dealt with and overcome and these include issues such as thermal sensitivity and destruction by heat, the formation of toxic byproducts, the high cost of operation, and the inefficiencies in the overall cycle duration. Consequently, healthcare agencies and industries have long needed a sterilizing technique that could function near room temperature and with much shorter times without inducing structural damage to a wide range of medical materials including various heat sensitive electronic components and equipment.

Atmospheric pressure plasmas for sterilization, as in the case of material processing, offer a number of distinct advantages to users. Its compact packaging makes it easily configurable, it eliminates the need for highly priced vacuum chambers and pumping systems, it can be installed in a variety of environments without additional facilitation needs, and its operating costs and maintenance requirements are minimal. In fact, the fundamental importance of atmospheric plasma sterilization lies in its ability to sterilize heat-sensitive objects, simple-to-use, and faster turnaround cycle. Atmospheric plasma sterilization may be achieved by the direct effect of reactive neutrals, including atomic oxygen and hydroxyl radicals, and plasma generated UV light, all of which can attack and inflict damage to bacteria cell membranes. Thus, there is a need for devices that can generate atmospheric pressure plasma as an effective and low-cost sterilization source.

One of the key factors that affect the efficiency of atmospheric plasma sterilization systems, as in the case of other plasma generating systems, is scalability of plasmas generated by the systems. There are several microwave nozzle based atmospheric pressure plasma systems widely used in the industrial and educational institutions around the world. The most of these designs are single nozzle based and they lack large volume scalability required for sterilization of medical devices applications. Also, such plasma systems generate high temperature plasma, which is not suitable for sterilization applications.

One solution to provide uniform plasma uses a nozzle array coupled to a microwave cavity. One of the challenging problems of such a system is controlling the microwave distribution within the microwave cavity so that the microwave energy (or, equivalently microwave) is localized at intended regions (hereinafter, referred to as "high-energy regions") that are stationary within the cavity. In such systems, plasma uniformity and scalability may be obtained by coupling nozzles to the controlled high-energy spots, which also enhances the operational efficiency of the system.

Most of the conventional systems having a microwave cavity are designed to provide a uniform microwave energy distribution in the microwave cavity. For example, Gerling, "WAVEGUIDE COMPONENTS AND CONFIGURATIONS FOR OPTIMAL PERFORMANCE IN MICROWAVE HEATING SYSTEMS," published on www.2450mhz.com by Gerling Applied Engineering Inc. in 2000, teaches a system having two rotating phase shifters. In this system, the two rotating phase shifters generate high-energy regions that continuously move within the microwave cavity to insure a uniform heating distribution within the microwave cavity.

In contrast to such conventional systems, a plasma generating system that has a plasma nozzle array should be able to deterministically control the microwave in its microwave cavity and generate high-energy regions coupled to the nozzle array. Thus, there is a strong need for plasma generating systems that can deterministically generate and control high-energy regions within the microwave cavity and have plasma nozzle arrays disposed so as to receive microwave energy from the high-energy regions.

SUMMARY OF THE INVENTION

The present invention provides various systems that have microwave plasma nozzle arrays and methods for configuring the plasma nozzle arrays.

According to one aspect of the present invention, a method for configuring a microwave plasma nozzle array, comprising the steps of: directing microwaves into a microwave cavity in opposing directions such that the microwaves interfere and form a standing microwave pattern that is stationary within the microwave cavity; adjusting a phase of at least one of the microwaves to control high-energy regions generated by the standing microwave pattern; and disposing a nozzle array at least partially in the microwave cavity so that each nozzle element of the nozzle array is disposed to receive microwave energy from a corresponding one of the high-energy regions of the standing microwave pattern.

According to one aspect of the present invention, a method for configuring a microwave plasma nozzle array, comprising: directing a first pair of microwaves into a microwave cavity in opposing directions along a first axis; directing a second pair of microwaves into the microwave cavity in opposing directions along a second axis, the first axis being normal to the second axis such that the first and the second pairs of microwaves interfere and form high-energy regions that are stationary within the microwave cavity; adjusting a phase of at least one of the microwaves to control the high-energy regions; and disposing a nozzle array at least partially in the microwave cavity so that each nozzle element of the nozzle array is configured to receive microwave energy from a corresponding one of the high-energy regions.

According to another aspect of the present invention, a microwave plasma nozzle array unit, comprising: a microwave cavity comprising a wall forming a portion of a gas flow channel; and an array of nozzles, each of the nozzles comprising: a gas flow tube adapted to direct a flow of gas therethrough and having an inlet portion and an outlet portion, the inlet portion being connected to the gas flow channel allowing communication between the gas flow tube and the gas flow channel; a rod-shaped conductor axially disposed in the gas flow tube, the rod-shaped conductor having a portion disposed in the microwave cavity to receive microwaves and a tapered tip positioned adjacent the outlet portion; and a vortex guide disposed between the rod-shaped conductor and the gas flow tube, the vortex guide having at least one passage for imparting a helical shaped flow direction around the rod-shaped conductor to a gas passing along the at least one passage.

According to still another aspect of the present invention, a microwave plasma system, comprising: a microwave source; a pair of isolators operatively connected to the microwave source; a microwave cavity having a pair of inlets and a wall forming a portion of a gas flow channel; a pair of waveguides, each of the waveguides being operatively connected to at least one of the isolators and to at least one of the inlets of the microwave cavity; a pair of non-rotating phase shifters, each of the non-rotating phase shifters being operatively connected to at least one of the waveguides and to at least one of the isolators; a pair of circulators, each of the circulators being operatively connected to at least one of the waveguides and being configured to direct microwaves to at least one of the non-rotating phase shifters; and an array of nozzles, each of the nozzles of the array comprising: a gas flow tube adapted to direct a flow of gas therethrough and having an inlet portion and an outlet portion, the inlet portion being connected to the gas flow channel allowing communication between the gas flow tube and the gas flow channel; a rod-shaped conductor being axially disposed in the gas flow tube, the rod-shaped conductor having a portion disposed in the microwave cavity to receive microwaves and a tapered tip positioned adjacent the outlet portion; and a vortex guide disposed between the rod-shaped conductor and the gas flow tube, the vortex guide having at least one passage for imparting a helical shaped flow direction around the rod-shaped conductor to a gas passing along the at least one passage.

According to yet another aspect of the present invention, a microwave plasma system, comprising: a microwave source; an isolator operatively connected to the microwave source; a microwave cavity having an inlet and a wall forming a portion of a gas flow channel; a waveguide operatively connected to the isolator and to the inlet of the microwave cavity; a non-rotating phase shifter operatively connected to the waveguide and the isolator; a circulator operatively connected to the waveguide and being configured to direct microwaves to the non-rotating phase shifter; a sliding short circuit operatively connected to the microwave cavity; and an array of nozzles, each of the nozzles of the array comprising: a gas flow tube adapted to direct a flow of gas therethrough and having an inlet portion and an outlet portion, the inlet portion being connected to the gas flow channel allowing communication between the gas flow tube and the gas flow channel; a rod-shaped conductor being axially disposed in the gas flow tube, the rod-shaped conductor having a portion disposed in the microwave cavity to receive microwaves and a tapered tip positioned adjacent the outlet portion; and a vortex guide disposed between the rod-shaped conductor and the gas flow tube, the vortex guide having at least one passage for imparting a helical shaped flow direction around the rod-shaped conductor to a gas passing along the at least one passage.

According to another aspect of the present invention, a microwave plasma system, comprising: a microwave source; a pair of isolators operatively connected to the microwave source; a microwave cavity having a pair of inlets and a wall forming a portion of a gas flow channel; a pair of waveguides, each of the waveguides being operatively connected to at least one of the isolators and to at least one of the inlets of the microwave cavity; a pair of non-rotating phase shifters, each of the non-rotating phase shifters being operatively connected to at least one of the waveguides and to at least one of the isolators; a pair of circulators, each of the circulators being operatively connected to at least one of the waveguides and being configured to direct microwaves to at least one of the non-rotating phase shifters; and a pair of sliding short circuits, each of the sliding short circuits being operatively connected to the microwave cavity; and an array of nozzles, each of the nozzles of the array comprising: a gas flow tube adapted to direct a flow of gas therethrough and having an inlet portion and an outlet portion, the inlet portion being connected to the gas flow channel allowing communication between the gas flow tube and the gas flow channel; a rod-shaped conductor being axially disposed in the gas flow tube, the rod-shaped conductor having a portion disposed in the microwave cavity to receive microwaves and a tapered tip positioned adjacent the outlet portion; and a vortex guide disposed between the rod-shaped conductor and the gas flow tube, the vortex guide having at least one passage for imparting a helical shaped flow direction around the rod-shaped conductor to a gas passing along the at least one passage.

According to another aspect of the present invention, a microwave plasma system, comprising: a microwave source; a microwave cavity having four inlets and a wall forming a portion of a gas flow channel; four waveguides, each of the waveguides being operatively connected to at least one of the inlets of the microwave cavity and the microwave source; four non-rotating phase shifters, each of the non-rotating phase shifters being operatively connected to at least one of the waveguides and the microwave source; four circulators, each of the circulators being operatively connected to at least one of the waveguides and being configured to direct microwaves generated by the microwave source to at least one of the non-rotating phase shifters; and an array of nozzles, each of the nozzles of the array comprising: a gas flow tube adapted to direct a flow of gas therethrough and having an inlet portion and an outlet portion, the inlet portion being connected to the gas flow channel allowing communication between the gas flow tube and the gas flow channel; a rod-shaped conductor being axially disposed in the gas flow tube, the rod-shaped conductor having a portion disposed in the microwave cavity to receive microwaves and a tapered tip positioned adjacent the outlet portion; and a vortex guide disposed between the rod-shaped conductor and the gas flow tube, the vortex guide having at least one passage for imparting a helical shaped flow direction around the rod-shaped conductor to a gas passing along the at least one passage.

These and other advantages and features of the invention will become apparent to those persons skilled in the art upon reading the details of the invention as more fully described below.

DETAILED DESCRIPTION OF THE PREFERRED EMBODIMENTS

As mentioned, conventional microwave plasma systems generate a uniform power distribution within a microwave cavity by controlling phase differences between two microwaves transmitted to the microwave cavity. Unlike existing systems, the present invention provides methods and systems for controlling the phases of the microwaves so that they can generate stationary high-energy regions within microwave cavities. Also methods for configuring a plasma nozzle array so as to use power from the high-energy regions are disclosed.

Figure 1:
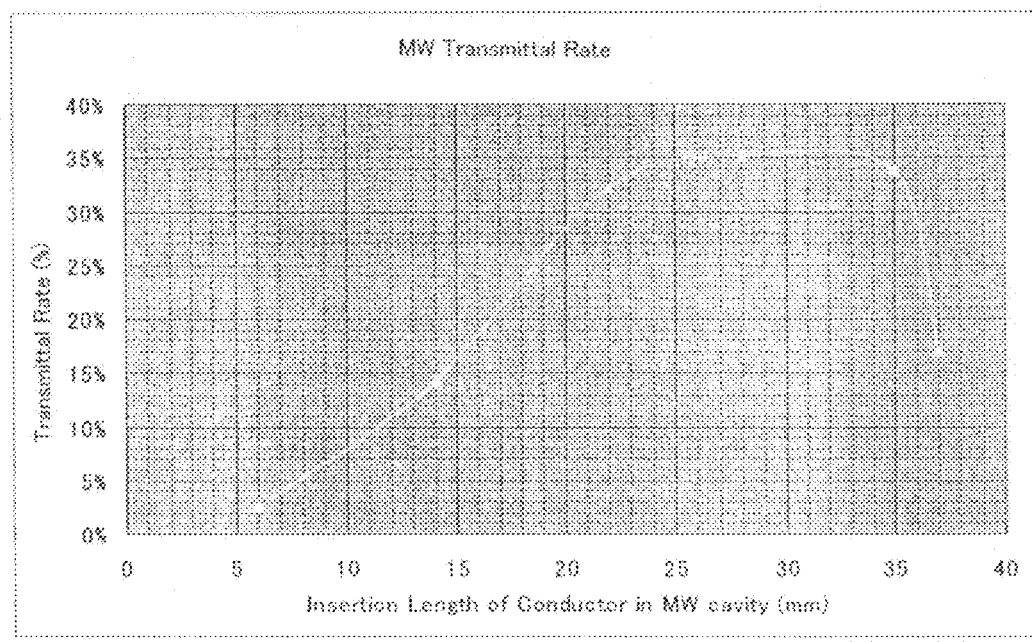
FIG. 1 is a schematic diagram of a system having a plasma nozzle array in accordance with one embodiment of the present invention.

FIG. 1 is a schematic diagram of a system 10 having a plasma nozzle array in accordance with one embodiment of the present invention. As illustrated, the system 10 comprises: a microwave source 13 having a microwave power head 12 that generates microwaves and a power splitter 14 having two outlets that split the microwaves generated by the microwave power head 12; a pair of isolators 17a and 17b configured to dissipate retrogressing microwaves that travel toward the microwave power head 12, each isolator including a dummy load 18a and 18b for dissipating the retrogressing microwaves and a circulator 16 for diverting the retrogressing microwaves to the corresponding dummy load 18a and 18b; a pair of non-rotating phase shifters 24a and 24b for shifting the phases of the microwaves; a pair of circulators 22a and 22b for directing microwaves from the power splitter 14 to the non-rotating phase shifters 24a and 24b, respectively; waveguides 20a and 20b for transmitting microwaves; and a microwave cavity 32. In one embodiment, the system 10 may further comprise: couplers 26a and 26b connected to power meters 28a and 28b for measuring microwave fluxes; and tuners 30a and 30b for matching impedance of microwaves. Typically, the microwave power head 12 includes a microwave generator and a power supply, which are not shown in FIG. 1 for simplicity. In another embodiment, an isolator may be located between the microwave power head 12 and the two-outlet power splitter 14, thereby replacing the pair of isolators 17a and 17b.

A nozzle array 37 comprising one or more nozzles 36a-n is connected to the microwave cavity 32 and generate plasma plumes 38a to 38n from a gas provided from a gas tank 34 through a mass flow control (MFC) valve 35. Several embodiments of the nozzles 36 and the microwave cavity 32 that may be used for the system 10 are discussed in copending U.S. patent application entitled "Microwave Plasma Nozzle with Enhanced Plume Stability and Heating Efficiency," filed on Jul. 7, 2004, which is hereby incorporated by reference in its entirety.

Figure 2A:
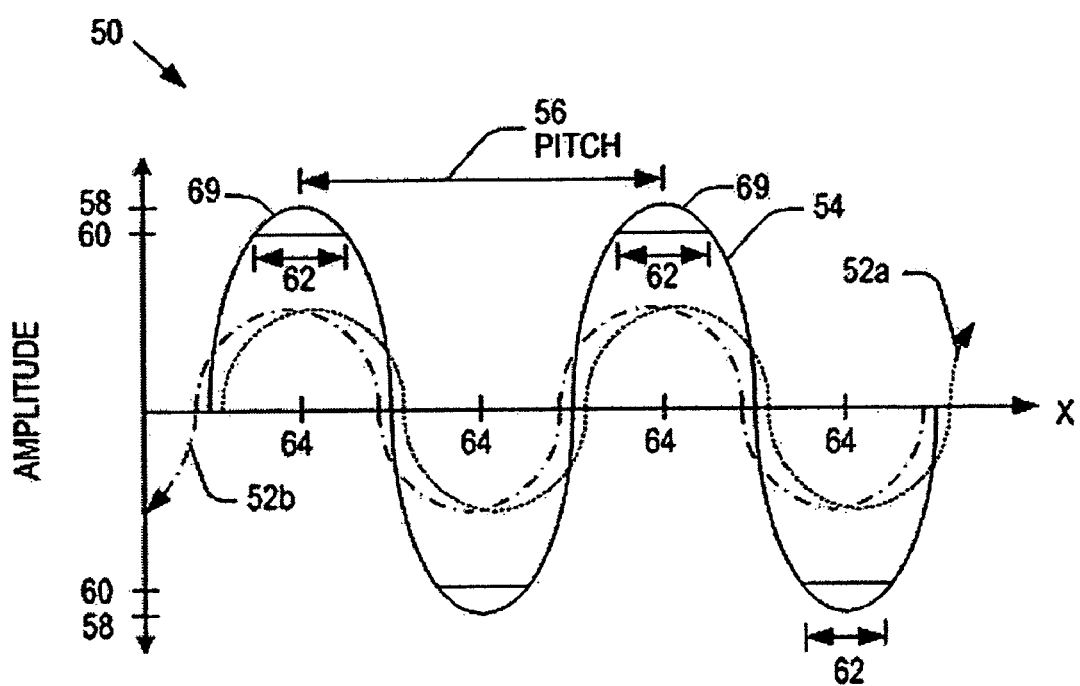
FIG. 2A schematically illustrates the interference of two microwaves within the microwave cavity of the system shown in FIG. 1, where the microwaves travel in opposing directions.

As shown schematically by waveforms 40a and 40b, microwaves transmitted from the power splitter 14 travel in opposing directions along an x-axis within the microwave cavity 32 and yield an interference pattern, as shown in FIG. 2A. FIG. 2A shows a plot 50 of microwaves 52a and 52b that interfere with each other to yield a standing microwave 54 within the microwave cavity 32. The abscissa and ordinate of the plot 50 represent the direction of microwave propagations and amplitude of microwaves, respectively. Since the intensity of the standing microwave 54 is proportional to the square of amplitude, the standing microwave 54 has peak locations 64 for each cycle where the amplitude reaches its maximum amplitude 58. (For simplicity, hereinafter, the amplitude refers to the absolute value of the amplitude.) The width 62 of high-energy regions 69 are shown where the amplitude of the standing microwave 54 exceeds a threshold 60 that may be set by a user.

Peak locations 64 and maximum amplitudes 58 of the peaks as well as the width 62 of the high-energy regions 69 may be controlled by the non-rotating phase shifters 24a and 24b, while a pitch 56 is determined by the wavelength of the microwaves 52a and 52b. If the phase difference between the microwaves 52a and 52b decreases, the maximum amplitude 58 and the width 62 of the high-energy regions 69 increase. If the phases of two microwaves 52a and 52b are shifted in one direction along the x-axis, the peak locations 64 may shift in that direction.

Figure 2B:
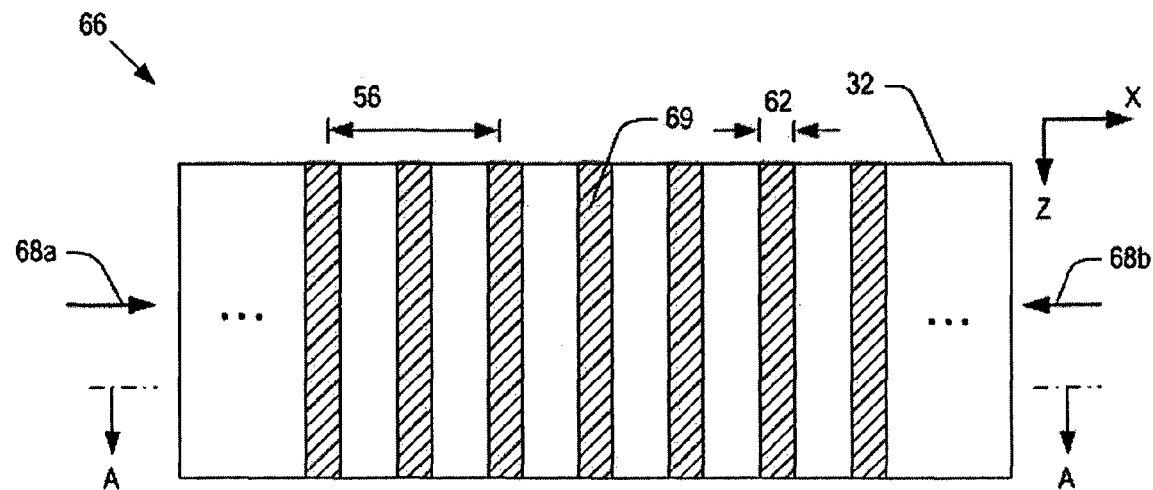
FIG. 2B schematically shows a distribution of high-energy regions within the microwave cavity for the system shown in FIG. 1.

FIG. 2B shows a distribution 66 of the high-energy regions 69 within the microwave cavity 32 viewed in a direction normal to the x-z plane. As shown in FIG. 2B, the high-energy regions 69 are generated by interference of the microwaves 52a and 52b propagating in the directions 68a and 68b, respectively, within the microwave cavity 32. As the microwaves 52a and 52b may be one-dimensional waves, each of the high-energy regions 69 may be in a rectangular strip shape and spaced by half of the pitch 56. In FIGS. 2A and 2B, the microwave cavity is assumed to be a rectangular parallelepiped for the purpose of illustration. However, it should be apparent to those of ordinary skill in the art that the microwave cavity can have any other shape without deviating from the present invention.

In an alternative embodiment, microwave source 13 may be replaced by two separate microwave power heads and two isolators attached thereto, respectively, where each microwave power head may transmit a microwave to the microwave cavity 32. In this embodiment, two microwaves 52a and 52b may have different wavelengths and amplitudes. However, by applying the same principle set forth above, the non-rotating phase shifters 24a and 24b can be used to control the peak locations 64 and the maximum amplitude 58 as well as the width 62 of high-energy regions 69.

Figure 3:
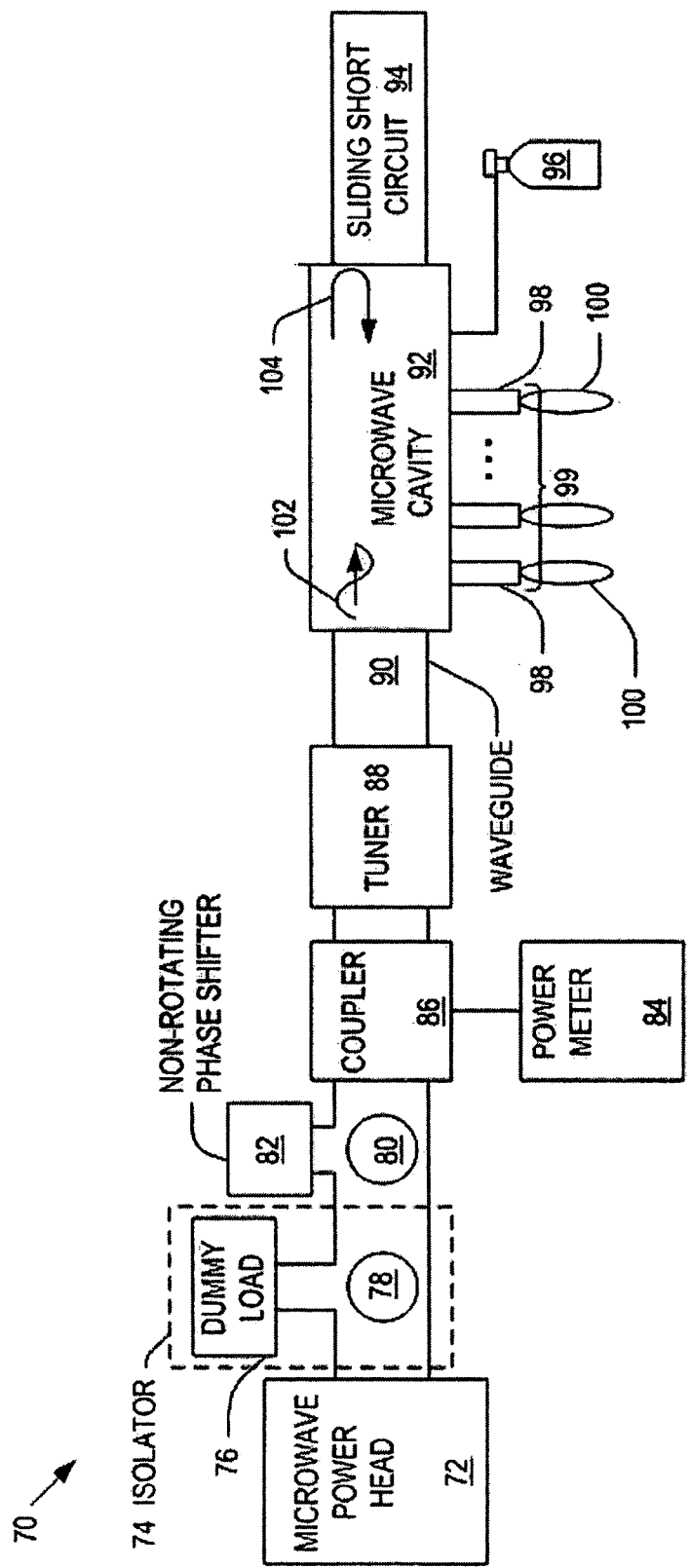
FIG. 3 is a schematic diagram of a system having a plasma nozzle array in accordance with another embodiment of the present invention.

FIG. 3 is a schematic diagram of a system 70 for deterministically generating high-energy regions within a microwave cavity in accordance with another embodiment of the present invention. As illustrated, the system 70 may include a microwave power head 72 for generating microwaves; an isolator 74 having a dummy load 76 configured to dissipate the retrogressing microwaves that propagate toward the microwave power head 72 and a circulator 78 for diverting the retrogressing microwave to a dummy load 76; a non-rotating phase shifter 82 for controlling a microwave phase; a circulator 80; a microwave cavity 92; a waveguide 90 for transmitting microwaves from the microwave power head 72 to the microwave cavity 92; and a sliding short circuit 94 for controlling the phase of the reflected microwaves. In one embodiment, the system 70 may further include a coupler 86 connected to power meters 84 for measuring microwave fluxes; and a tuner 88 for matching the impedance of the microwaves. In another embodiment, the sliding short circuit 94 may be replaced by a wall, where the dimensions of the microwave cavity 92 along the microwave propagation is a multiple of half a wavelength of the microwaves. A nozzle array 99 comprising nozzles 98 may be connected to the microwave cavity 92 and generate plasma plumes 100 from a gas provided from a gas tank 96. The specific details of the nozzles 98 will be discussed below.

In FIG. 3, an inset diagram 102 illustrates the propagation of microwaves transmitted from the microwave power head 72 to the microwave cavity 92. The transmitted microwaves are reflected from the sliding short circuit 94, as indicated by an arrow 104, and they interfere with the incoming microwaves to generate standing microwaves within the microwave cavity 92. The sliding short circuit 94 can control the phase of the reflected microwaves and, if it is used in conjunction with a non-rotating phase shifter 82, control the locations and the maximum amplitude of the standing waves as well as the width of high-energy regions that are similar to the high-energy regions 69 shown in FIG. 2B.

Figure 4A:
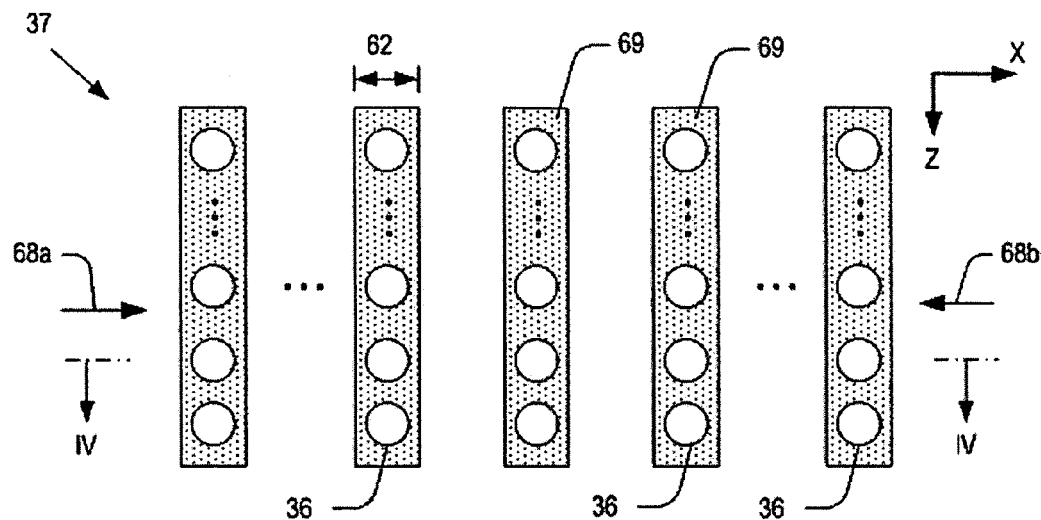
FIG. 4A shows a top view of the plasma nozzle array shown in FIG. 1.

FIG. 4A shows a top view of the nozzle array 37 in FIG. 1, illustrating the nozzles 36 located within the high-energy regions 69 established within the microwave cavity 32 by microwaves traveling in opposing directions 68a and 68b. In FIG. 4A, the nozzle array 37 is described as a two-dimensional array. However, it should be apparent to those of ordinary skill that other arrangements of nozzles may be used. For example, the nozzle array 37 may have only a one-dimensional array of the nozzles 36 arranged in either the z-direction or the x-direction. It is noted that a nozzle array 99 in FIG. 3 may have the same arrangement as shown in FIG. 4A.

Figure 4B:
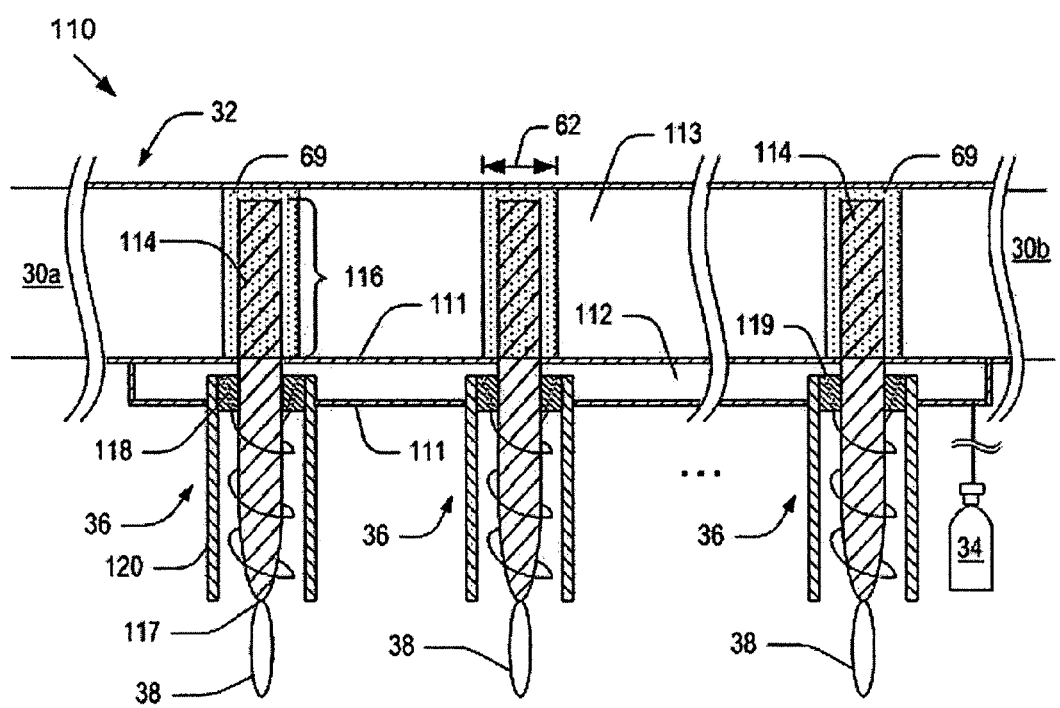
FIG. 4B shows a cross-sectional view of the microwave cavity and the nozzle array shown in FIG. 1 taken along line IV-IV.

FIG. 4B shows a cross-sectional diagram 110 of the microwave cavity 32 and the nozzles 36, collectively shown by reference number 110, taken along a direction IV-IV of FIG. 4A. As shown in FIG. 4B, the microwave cavity 32 includes a wall 111 that forms a gas flow channel 112 for admitting a gas from the gas tank 34; and a cavity 113 for receiving microwaves transmitted from the microwave source 13 and generating the high-energy regions 69. Each nozzle 36 includes a gas flow tube 120 connected to the cavity wall 111 to receive a gas through the gas flow channel 112; a rod-shaped conductor 114 having a portion 116 for collecting microwaves from the high-energy regions 69 in the cavity 113; and a vortex guide 118 disposed between the rod-shaped conductor 114 and the gas flow tube 120. The vortex guide 118 has at least one opening 119 for producing a helical swirl flow path around the rod-shaped conductor 114. The microwaves received by the rod-shaped conductor portion 116 are focused on its tapered tip 117 to generate the plasma plumes 38 using the gas.

The width 62 of the high-energy regions 69 may be optimized by controlling the non-rotating phase shifters 24a and 24b. In general, a smaller width of high-energy regions 69 may yield a higher operational efficiency of the nozzles 36. However, considering the potential variation of the high-energy regions 69 during operation of the system 10, the width 62 of the high-energy regions 69 may be slightly larger than the diameter of the rod-shaped conductor 114.

Figure 4C:
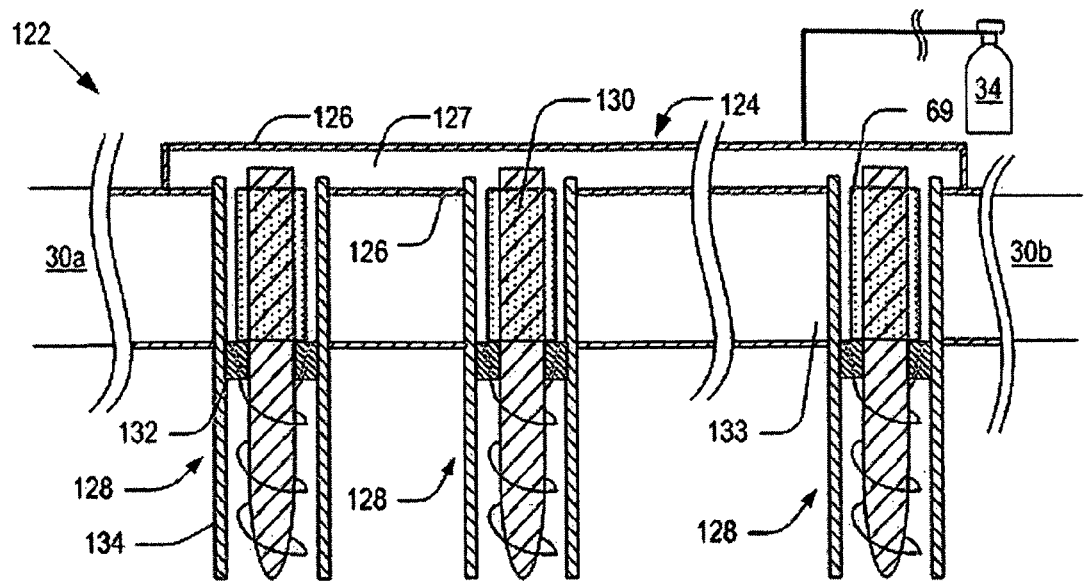
FIG. 4C shows a cross-sectional view of another embodiment of the microwave cavity and the nozzle array shown in FIG. 1.

FIG. 4C shows a cross-sectional view of an alternative embodiment of a microwave cavity 124 and nozzle array 122 similar to the microwave cavity and the nozzle array shown in FIG. 4B. As illustrated, a nozzle 128 has similar components as that shown in FIG. 4B. FIG. 4C includes a gas flow tube 134 sealingly connected to a wall 126 to a receive a gas through a gas flow channel 127; a rod-shaped conductor 130 for collecting microwaves from the high-energy regions 69 in a cavity 133; and a vortex guide 132. In one embodiment, the gas flow tube 134 may be made of any material that is substantially transparent to microwaves (i.e., microwaves can pass through the gas flow tube 134 with very low loss of energy) and, as a consequence, the gas flowing through the gas flow tube 134 may be pre-heated within the cavity 133 prior to reaching the region of the tapered tip of the rod-shaped conductor 130.

Figure 4D:
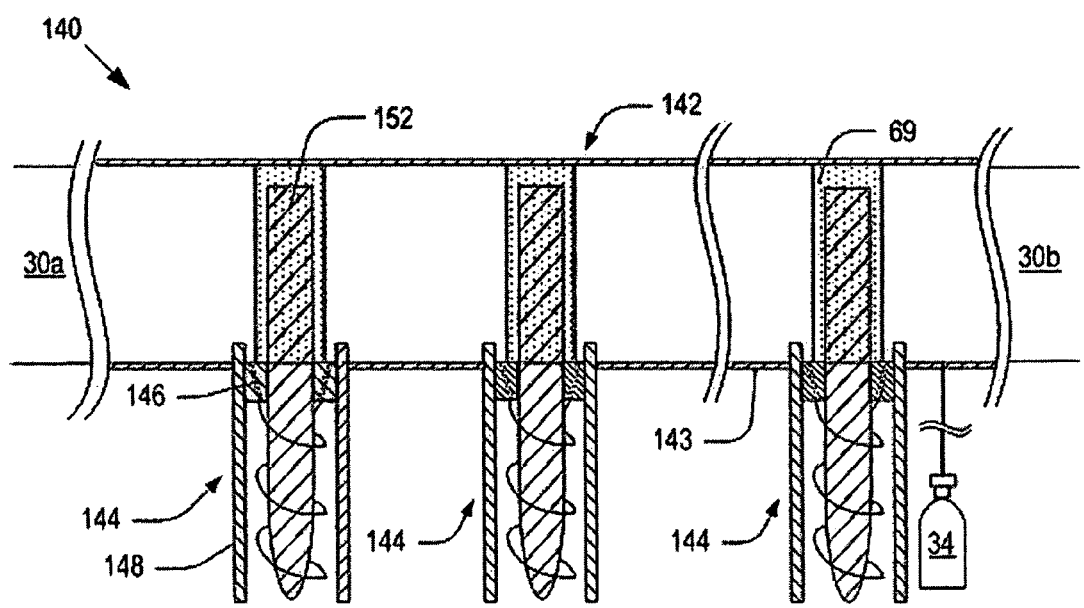
FIG. 4D shows a cross-sectional view of still another embodiment of the microwave cavity and the nozzle array shown in FIG. 1.

FIG. 4D shows a cross-sectional view of an alternative embodiment of a microwave cavity and nozzle array 140 similar to the microwave cavity and the nozzle array shown in FIG. 4B. As illustrated, nozzles 144 have components similar to their counterparts in FIG. 4B: a gas flow tube 148 sealingly connected to a wall 143 of a microwave cavity 142 to receive a gas; a rod-shaped conductor 152 for collecting microwaves from the high-energy regions 69; and a vortex guide 146. In one embodiment, the microwave cavity 142 may form a gas flow channel connected to the gas tank 34.

FIG. 4D includes the rod-shaped conductor 152 which is similar to the conductor 114 illustrated in FIG. 4B where the portion 116 of the rod-shaped conductor 114 is inserted into the cavity 113 to receive microwaves. Then, the received microwaves travel along the surface thereof and are focused on the tapered tip. Since a portion of the traveling microwaves may be lost through the gas flow tube, a shielding mechanism may be used to enhance the efficiency of the nozzles, which are illustrated in FIGS. 5A-5B.

Figure 5C:
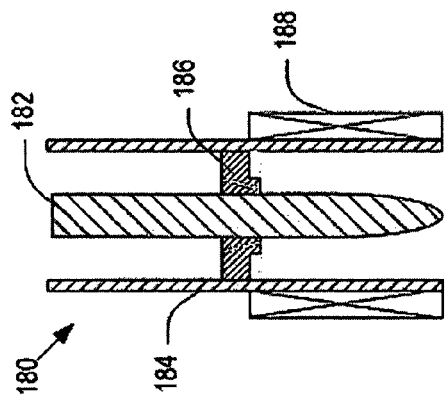
FIGS. 5A-5F show cross-sectional views of alternative embodiments of the microwave plasma nozzle shown in FIG. 4B, illustrating additional components for enhancing nozzle efficiency.
Figure 5F:
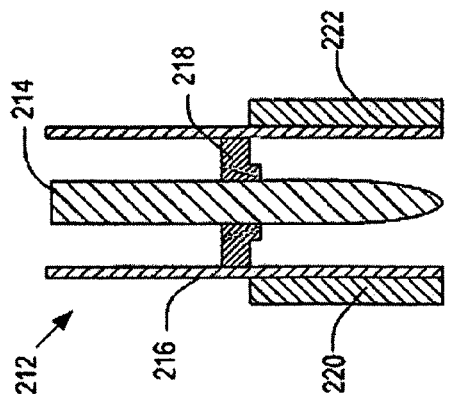
Figure 5B:
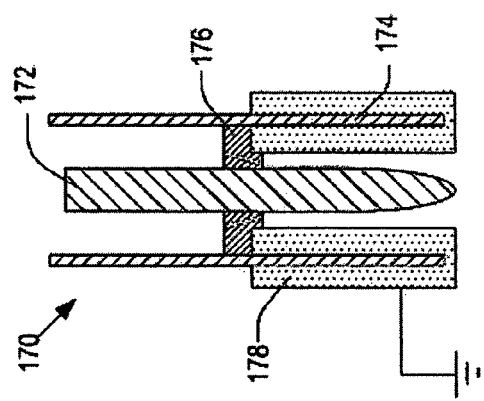
Figure 5E:
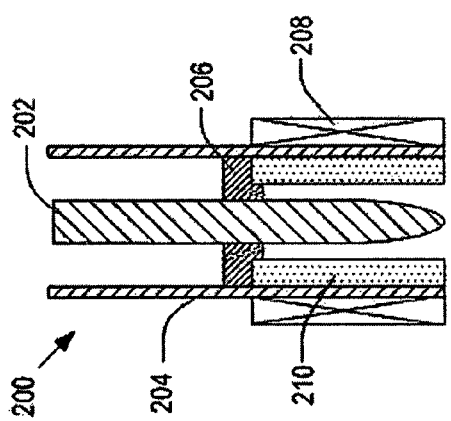
Figure 5A:
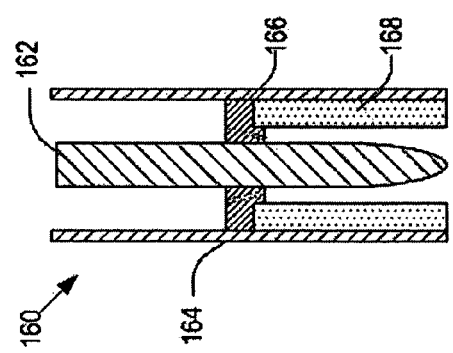

FIG. 5A shows a cross-sectional view of a nozzle 160 which is an alternative embodiment of the nozzle 36 shown in FIG. 4B. As illustrated in FIG. 5A, the nozzle 160 includes: a rod-shaped conductor 162; a gas flow tube 164; a vortex guide 166; and an inner shield 168 for reducing microwave loss through the gas flow tube 164. In one embodiment, the inner shield 168 has a tubular shape and engages a recess formed along an outer surface of the vortex guide 166. The inner shield 168 may provide additional control of the helical swirl around the rod-shaped conductor 162 and increase the plasma stability by changing the gap between the gas flow tube 164 and the rod-shaped conductor 162.

FIG. 5B is a cross-sectional view of another nozzle 170 which is similar to the nozzle 36 shown in FIG. 4B. As illustrated in FIG. 5B, the nozzle 170 includes: a rod-shaped conductor 172; a gas flow tube 174; a vortex guide 176; and a grounded shield 178 for reducing microwave power loss through the gas flow tube 174. The grounded shield 178 may cover a portion of the gas flow tube 174 that is outside of the microwave cavity. Like the inner shield 168, the grounded shield 178 may provide the additional control of the helical swirl around the rod-shaped conductor 172 and increase the plasma stability by changing the gap between the gas flow tube 174 and the rod-shaped conductor 172.

As mentioned above, the main heating mechanism applied to the nozzles shown in FIGS. 4B-4D are the microwaves that are focused and discharged adjacent the tapered tip of the rod-shaped conductor, where the nozzles may produce non-LTE plasmas for sterilization. In non-LTE plasmas, the temperature of ions and neutral species may be less than 100° C., while the temperature of electrons can be up to several tens of thousand degrees in Celsius. Thus, such plasmas are highly electronically excited. To enhance the electronic temperature and increase the nozzle efficiency, the nozzles may include additional mechanisms that electronically excite the gas while the gas is within the gas flow tube, as illustrated in FIGS. 5C-5F.

FIG. 5C is a cross-sectional view of yet another nozzle 180 which is similar to the nozzle 36 shown in FIG. 4B. As illustrated in FIG. 5C, the nozzle 180 includes: a rod-shaped conductor 182; a gas flow tube 184; a vortex guide 186; and a pair of outer magnets 188 for electronic excitation of the swirling gas in the gas flow tube 184. In one embodiment, each of the outer magnets 188 has a cylindrical shell having a semicircular cross section disposed around the outer surface of the gas flow tube 184.

Figure 5D:
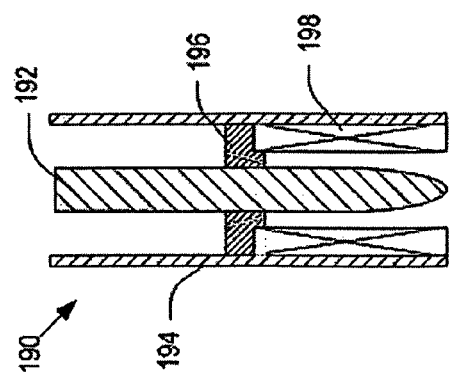

FIG. 5D shows a cross-sectional view of still another nozzle 190. As shown in FIG. 5D, the nozzle 190 includes: a rod-shaped conductor 192; a gas flow tube 194; a vortex guide 196; and a pair of inner magnets 198, secured by the vortex guide 196 within the gas flow tube 194, for electronic excitation of the helical swirl in the gas flow tube 194. In one embodiment, each of the inner magnets 198 has a cylindrical shell having a semicircular cross section.

FIG. 5E shows a cross-sectional view of still another nozzle 200. As shown in FIG. 5E, the nozzle 200 includes: a rod-shaped conductor 202; a gas flow tube 204; a vortex guide 206; a pair of outer magnets 208; and an inner shield 210. In one embodiment, each of the outer magnets 208 has a cylindrical shell having a semicircular cross section. In another embodiment, the inner shield 210 may have a tubular shape.

FIG. 5F is a cross-sectional view of another nozzle 212. As illustrated in FIG. 5F, the nozzle 212 includes: a rod-shaped conductor 214; a gas flow tube 216; a vortex guide 218; an anode 220; and a cathode 222. The anode 220 and the cathode 222, connected to an electrical power source (not shown in FIG. 5F for simplicity), may electronically excite the swirling gas in the gas flow tube 216.

As mentioned above, FIGS. 5A-5F show cross-sectional views of various embodiments of the nozzle 36 shown in FIG. 4B. However, it should be apparent to one of ordinary skill that the similar sets of alternative embodiments shown in FIGS. 5A-5F can be applied to the nozzles shown in FIGS. 4C and 4D. Also, one skilled in the art will appreciate that the descriptions in FIGS. 4A-5F may be equally applied to the system 70 in FIG. 3.

Referring back to FIG. 2B, the nozzles 36 may be configured within the high-energy regions 69 to maximize the use of microwave energy within the microwave cavity 32. In general, operational efficiency of the microwave cavity 32 may increase if the high-energy regions 69 are confined only around the nozzles 36. As the cross section of a typical nozzle is circular or rectangular with an aspect ratio of a near unity, operational efficiency of the microwave cavity may be maximized if the high-energy regions are confined within rectangular regions in a 2-dimensional matrix form as will be described in FIGS. 6-8.

Figure 6:
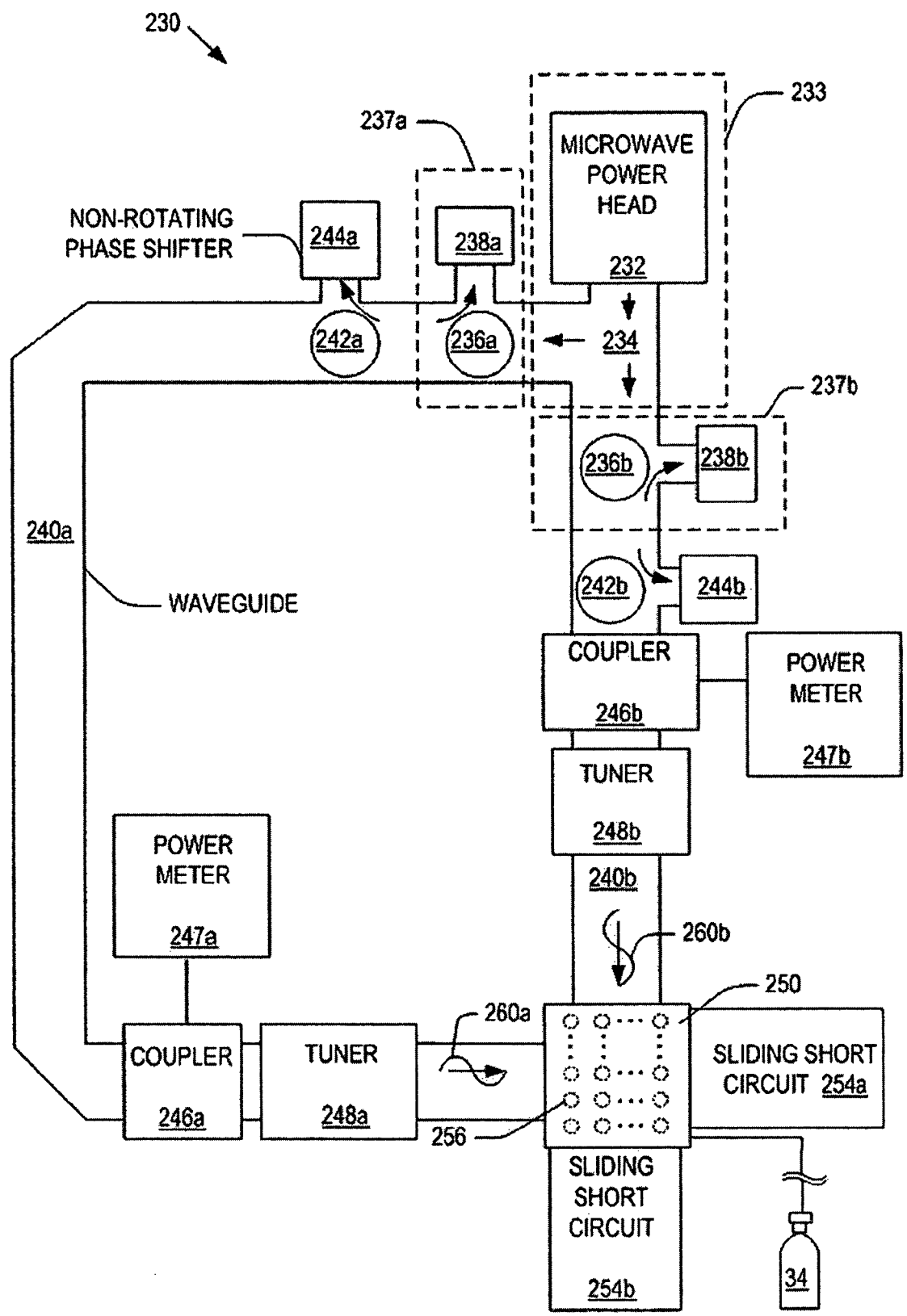
FIG. 6 is a schematic diagram of a system having a plasma nozzle array in accordance with another embodiment of the present invention.

FIG. 6 shows a schematic diagram of a system 230 having a plasma nozzle array in accordance with one embodiment of the present invention. The components of the system 230 are similar to their counterparts of FIG. 1, except that the microwaves are traveling normal to each other in a microwave cavity 250. As illustrated, the system 230 includes: a microwave source 233 that has a microwave power head 232 and a power splitter 234 having two outlets; a pair of non-rotating phase shifters 244a and 244b; a pair of isolators 237a and 237b including a pair of circulators 236a and 236b and a pair of dummy loads 238a and 238b; a pair of circulators 242a and 242b; waveguides 240a and 240b; the microwave cavity 250; one or more nozzles 256, preferably forming a two-dimensional array; and a pair of sliding short circuits 254a and 254b. Inset diagrams 260a and 260b represent microwaves transmitted to the microwave cavity 250. In one embodiment, the system 230 may further include: a pair of couplers 246a and 246b; a pair of tuners 248a and 248b; and a pair of power meters 247a and 247b connected to a pair of couplers 246a and 246b, respectively. The gas tank 34 may be connected to the microwave cavity 250 to provide a gas to the nozzles 256 that are coupled to the microwave cavity 250. In another embodiment, an isolator may be located between the microwave power head 232 and the power splitter 234, replacing the isolators 237a and 237b.

Figure 7:
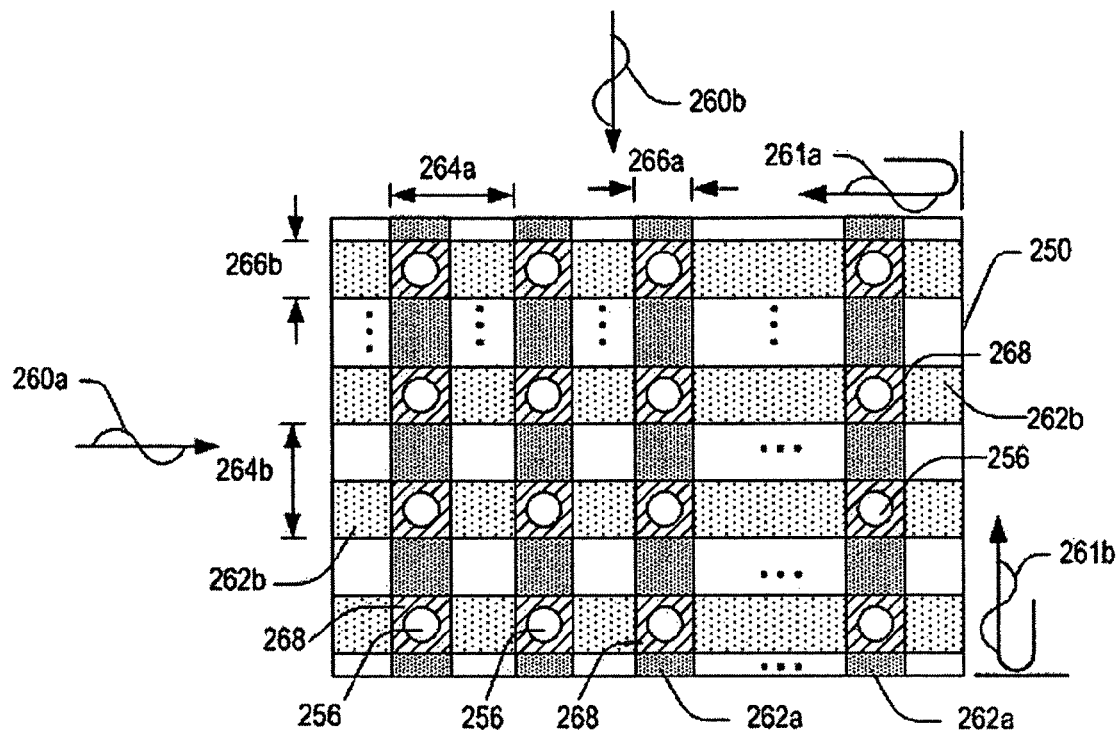
FIG. 7 schematically illustrates an interference a pattern of the high-energy regions found within the microwave cavity of the system shown in FIG. 6, illustrating the arrangement of the nozzle array in the high-energy regions.

FIG. 7 shows a distribution of high-energy regions within the microwave cavity 250 viewed in a direction normal to a plane defined by the propagation directions of two interfering microwaves. As shown in FIG. 7, two microwaves, shown schematically waveforms 260a and 260b, and two reflected microwaves, shown schematically by waveforms 261a and 261b, generate high-energy regions 268 in a two-dimensional array form, where intervals 264a and 264b correspond to half-wavelengths of the microwaves 260a and 260b, respectively. By the same principle as applied to the interference pattern shown in FIG. 2B, the microwaves 260a and 261a, and the microwaves 260b and 261b, generate two standing microwaves that yield strip-shaped high-energy regions 262a and 262b, respectively. Then, the standing microwaves may further interfere to generate high-energy regions 268 in a matrix form as shown in FIG. 7. Locations and widths 266a and 266b of the high-energy regions may be controlled by the non-rotating phase shifters 244a and 244b and/or the sliding short circuits 254a and 254b. A portion of a rod-shaped conductor of each nozzle 256 may be located within the high-energy regions to collect the microwave energy, as illustrated in FIG. 7.

In an alternative embodiment, two separate microwave power heads may replace the microwave source 233, where each microwave power head may transmit microwaves to the microwave cavity 250. In such embodiment, two microwaves may have different wavelengths and amplitudes, and as a consequence, the intervals 264a and 264b may be different from each other. Likewise, the widths 266a and 266b of the high-energy regions may be different from each other.

Figure 8:
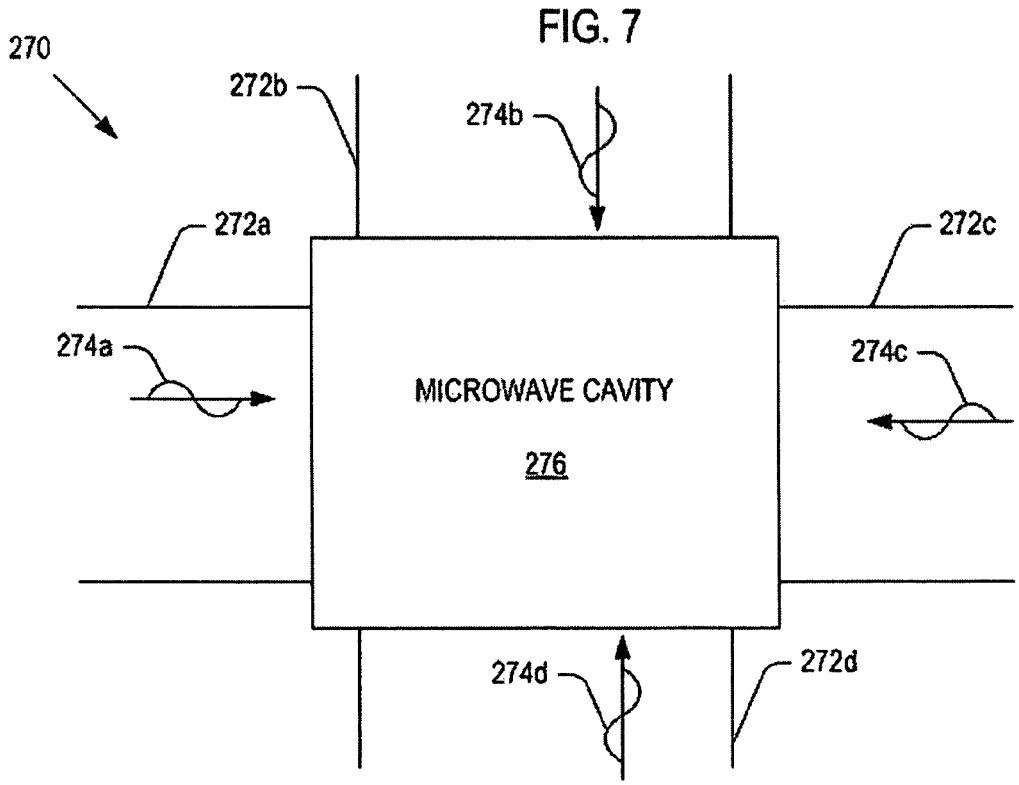
FIG. 8 is a schematic diagram of a microwave cavity and waveguides for generating high-energy regions in a two-dimensional array form in accordance with another embodiment of the present invention.

FIG. 8 is a schematic diagram of a microwave cavity and waveguides 270 for generating the high-energy regions in a two-dimensional array form in accordance with another embodiment of the present invention. As illustrated in FIG. 8, a microwave cavity 276 may receive four microwaves 274a to 274d traveling through four waveguides 272a to 272d, respectively. The phases of the microwaves may be controlled by a corresponding one of four non-rotating phase shifters (not shown in FIG. 8) coupled to the waveguides 272a to 272d, respectively. The four microwaves 274a to 274d may be generated by one or more microwave power heads. In one embodiment, each of four microwaves 274a to 274d may be generated by a corresponding one of the four microwave power heads, respectively. In another embodiment, two microwave power heads generate microwaves, where each microwave is split into two microwaves. In further embodiment, one microwave power head may be split into four microwaves using a power splitter having four outlets. It is noted that these three embodiments are provided for exemplary purposes only. Thus, it should be apparent to one of ordinary skill that a system with the capability to provide four microwaves may be connected to the microwave waveguides 272a to 272d without deviating from the present invention.

Various embodiments of nozzles in FIGS. 5A-5F and walls of microwave cavities in FIG. 4B-4D that form gas flow channels may be equally applied to the systems described in FIG. 8. For simplicity, such embodiments have not been shown.

Figure 9:
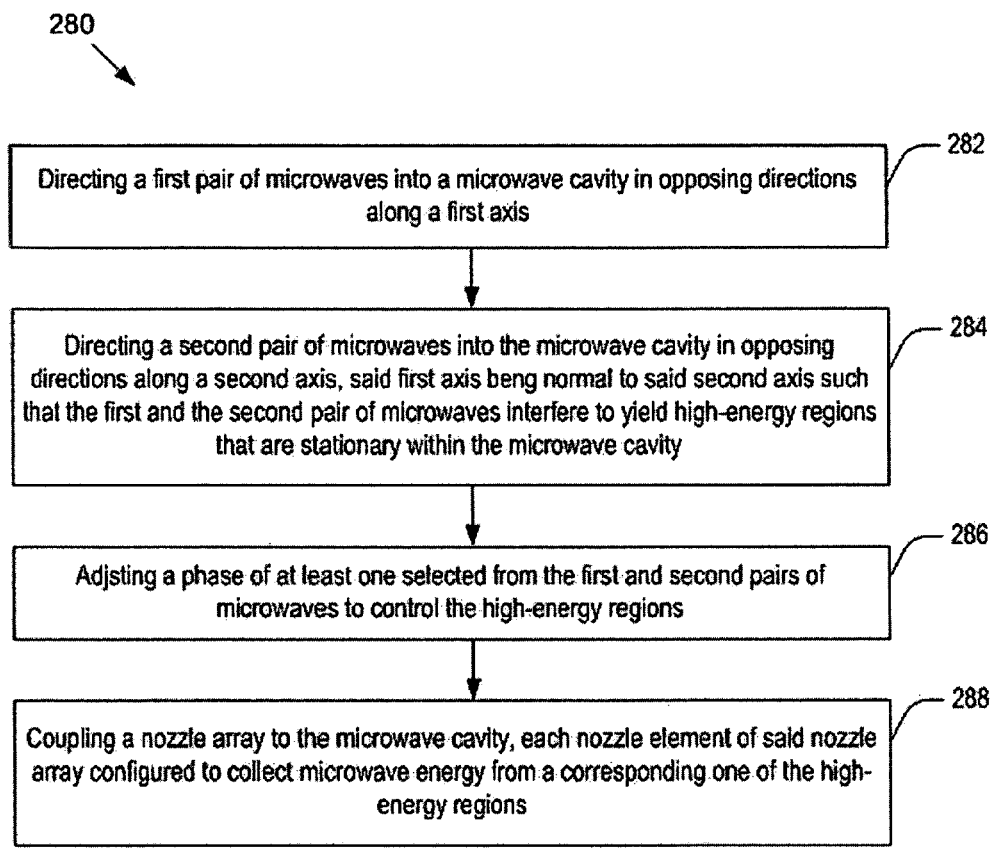
FIG. 9 shows a flowchart illustrating the exemplary steps for generating and controlling a microwave plasma nozzle array in accordance with at least one embodiment of the present invention.

FIG. 9 shows a flowchart 280 illustrating the exemplary steps for configuring a microwave plasma nozzle array in accordance with one embodiment of the present invention. At step 282, the first pair of microwaves is directed into a microwave cavity in opposing directions along a first axis. Next, at step 284, the second pair of microwaves is directed into the microwave cavity in opposing directions along a second axis, where the first axis is normal to the second axis such that the first and the second pairs of microwaves interfere to yield high-energy regions that are stationary within the microwave cavity. Then, a phase of at least one microwave selected from the first and second pair of microwaves is adjusted to control the high-energy regions at step 286. Finally, at step 288, a nozzle array is coupled to the microwave cavity, where each nozzle element of the nozzle array is configured to collect the microwave energy from a corresponding one of the high-energy regions.

While the present invention has been described with a reference to the specific embodiments thereof, it should be understood, of course, that the foregoing relates to preferred embodiments of the invention and that modifications may be made without departing from the spirit and the scope of the invention as set forth in the following claims.

In addition, many modifications may be made to adapt a particular situation, systems, process, process step or steps, to the objective, the spirit and the scope of the present invention. All such modifications are intended to be within the scope of the claims appended hereto.

What is claimed is:

1. A method for generating plasma plumes through a microwave plasma nozzle array, comprising the steps of:
   directing microwaves into a microwave cavity in opposing directions such that the microwaves interfere with each other and form a standing microwave pattern that is stationary within the microwave cavity;
   adjusting a phase of at least one of the microwaves to form high-energy regions in the standing microwave pattern, the high-energy regions having a width where an amplitude of the microwaves exceeds a threshold value;
   providing an array of nozzles, each of the nozzles including:
   a rod-shaped conductor having a first end and a second end where the first end being a leading end of the rod-shaped conductor, and
   a gas flow tube having a first end portion disposed inside the microwave cavity and a second end portion disposed outside of the microwave cavity, the first end portion is made of a substantially microwave transparent material and further the gas flow tube surrounds at least a part of the rod-shaped conductor in such a manner that the second end portion is in proximity to the first end of the rod-shaped conductor, and a portion of the gas flow tube is connected to the microwave cavity at a location where the gas flow tube surrounds the rod-shaped conductor; and
   disposing the array of nozzles in the microwave cavity such that a middle portion of the rod-shaped conductor is held with respect to said gas flow tube via a holding member, at least the second end of each of the rod-shaped conductors is disposed in the microwave cavity to receive microwave energy from a corresponding one of the high-energy regions of the standing microwave pattern; the first end is being outside the microwave cavity and the second end is suspended free in the microwave cavity in such a manner that the second end is free from contact with any walls forming the microwave cavity and any members that are in contact with said walls of the microwave cavity so that plasma is formed outside of the microwave cavity.

2. A method as defined in claim 1, wherein said step of directing microwaves includes the steps of:
   transmitting microwaves to the microwave cavity; and
   reflecting microwaves using a sliding short circuit operatively connected to the microwave cavity.

3. A method as defined in claim 1, wherein said step of directing microwaves includes the step of:
   transmitting microwaves generated by two microwave power heads to the microwave cavity via respective waveguides, and
   introducing the microwaves into the microwave cavity directly from opposite sides of the cavity.

4. A method as defined in claim 1, wherein said step of adjusting a phase of at least one of the microwaves includes forming the high-energy regions in a striped pattern so that the nozzles are located within the high-energy regions.

5. A method as defined claim 1, wherein said step of providing an array of nozzles includes providing each of the conductors with a portion for collecting the microwaves and a tapered tip for focusing the microwaves to generate the plasma plumes.

6. A method for generating plasma plumes through a microwave plasma nozzle array as defined in claim 1,
wherein each of said nozzles includes an inner shield disposed around the inner surface of the gas flow tube to reduce microwave loss through the gas flow tube.

7. The method as defined in claim 1, wherein one end of the gas flow tube projects externally from the microwave cavity.

8. A method for generating plasma plumes through a microwave plasma nozzle array, comprising the steps of:
directing a first pair of microwaves into a microwave cavity in opposing directions along a first axis;
directing a second pair of microwaves into the microwave cavity in opposing directions along a second axis, the first axis being normal to the second axis such that the first and the second pairs of microwaves cross and interfere with each other to form high-energy regions that are arranged in a matrix pattern and are stationary within the microwave cavity;
adjusting a phase of at least one of the microwaves to control the high-energy regions, the high-energy regions having a width where an amplitude of the microwaves exceeds a threshold value;
providing a plurality of nozzles, each of the nozzles including:
a rod-shaped conductor having a first end and a second end where the first end being a leading end of the rod-shaped conductor, and
a gas flow tube having a first end portion disposed inside the microwave cavity and a second end portion disposed outside of the microwave cavity, the first end portion is made of a material which is substantially transparent to microwaves and further the gas flow tube surrounds at least part of the rod-shaped conductor in such a manner that the second end portion is in proximity to the first end of the rod-shaped conductor, and a portion of the gas flow tube is connected to the microwave cavity at a location where the gas flow tube surrounds the rod-shaped conductor; and
disposing a plurality of nozzle arrays in the microwave cavity such that a middle portion of the rod-shaped conductor is held with respect to said gas flow tube via a holding member, at least the second end of each of the rod-shaped conductors in each nozzle is disposed in the microwave cavity so that each nozzle element of the nozzle arrays is configured to receive microwave energy from a corresponding one of the high-energy regions; the first end is being outside the microwave cavity and the second end is suspended free in the microwave cavity in such a manner that the second end is free from contact with any walls forming the microwave cavity and any members that are in contact with said walls of the microwave cavity so that plasma is formed outside of the microwave cavity.

9. A method as defined in claim 8, wherein said step of directing the first pair of microwaves includes the steps of:
transmitting microwaves to the microwave cavity; and
reflecting microwaves using a sliding short circuit operatively connected to the microwave cavity.

10. A method as defined in claim 8, wherein each of said step of directing the first pair of microwaves and said step of directing the second pair of microwaves includes the step of:
transmitting microwaves generated by two microwave power heads to the microwave cavity, via respective waveguides, and
introducing the microwaves into the microwave cavity directly from opposite sides of the cavity.

11. A method as defined in claim 8, further comprising the steps of:
generating the microwaves by a microwave power head; and
providing a power splitter connected to the microwave power head.

12. A method as defined in claim 8, wherein said step of adjusting a phase of at least one of the microwaves includes adjusting phases of the first pair of microwaves.

13. A method as defined in claim 8, wherein said step of adjusting a phase of at least one of the microwaves includes adjusting phases of the second pair of microwaves.

14. A method as defined in claim 8, wherein said step of adjusting a phase of at least one of the microwaves includes adjusting phases of both the first pair and the second pair of microwaves.

15. A method for generating plasma plumes through a microwave plasma nozzle array as defined in claim 8,
wherein each of said nozzles includes an inner shield disposed around the inner surface of the gas flow tube to reduce microwave loss through the gas flow tube.

16. The method as defined in claim 8, wherein one end of the gas flow tube projects externally from the microwave cavity.

17. A method for generating plasma plumes through a microwave plasma nozzle array, comprising the steps of:
directing microwaves into a microwave cavity in opposing directions through separate waveguides such that the microwaves are injected into the microwave cavity via two opposite openings formed on a wall of the microwave cavity, interfere and form a standing microwave pattern that is stationary within the microwave cavity;
adjusting a phase of at least one of the microwaves to control high-energy regions generated by the standing microwave pattern, the high-energy regions having a width where an amplitude of the microwaves exceeds a threshold value;
providing a plurality of nozzles, each of the nozzles including:
a rod-shaped conductor having a first end and a second end where the first end being a leading end of the rod-shaped conductor, and
a gas flow tube having a first end portion disposed inside the microwave cavity and a second end portion disposed outside of the microwave cavity, the first end portion is made of a material substantially transparent to microwaves and further the gas flow tube surrounds at least part of the rod-shaped conductor in such a manner that the second end portion is in proximity to the first end of the rod-shaped conductor, and a portion of the gas flow tube is connected to the microwave cavity at a location where the gas flow tube surrounds the rod-shaped conductor; and
disposing the nozzle array at least partially in the microwave cavity so that a middle portion of the rod-shaped conductor is held with respect to said gas flow tube via a holding member, at least the second end of the rod-shaped conductor is disposed in the microwave cavity to receive microwave energy from a corresponding one of the high-energy regions of the standing microwave pattern; the first end is being outside the microwave cavity and the second end is suspended free in the microwave cavity in such a manner that the second end is free from contact with any walls forming the microwave cavity and any members that are in contact with said walls of the microwave cavity so that plasma is formed outside of the microwave cavity.

18. A method for generating plasma plumes through a microwave plasma nozzle array as defined in claim 17, wherein each of said nozzles includes an inner shield disposed around the inner surface of the gas flow tube to reduce microwave loss through the gas flow tube.

19. The method as defined in claim 17, wherein one end of the gas flow tube projects externally from the microwave cavity.

* * * * *